US011292917B2

(12) United States Patent
Wosylus et al.

(10) Patent No.: US 11,292,917 B2
(45) Date of Patent: Apr. 5, 2022

(54) GOLDEN EFFECT PIGMENTS

(71) Applicant: BASF Colors & Effects GmbH, Ludwigshafen am Rhein (DE)

(72) Inventors: Aron Wosylus, Ludwigshafen (DE); Heinrich Woelk, Ludwigshafen (DE); Raimund Schmid, Ludwigshafen (DE); Stefan Wrobel, Besigheim (DE)

(73) Assignee: BASF Colors & Effects GmbH, Ludwigshafen am Rhein (DE)

( * ) Notice: Subject to any disclaimer, the term of this patent is extended or adjusted under 35 U.S.C. 154(b) by 151 days.

(21) Appl. No.: 16/639,920

(22) PCT Filed: Sep. 19, 2018

(86) PCT No.: PCT/EP2018/075289
§ 371 (c)(1),
(2) Date: Feb. 18, 2020

(87) PCT Pub. No.: WO2019/063372
PCT Pub. Date: Apr. 4, 2019

(65) Prior Publication Data
US 2020/0239698 A1     Jul. 30, 2020

(30) Foreign Application Priority Data
Sep. 26, 2017   (EP) .................................... 17193224

(51) Int. Cl.
| C09C 3/06 | (2006.01) |
| C09D 157/00 | (2006.01) |
| C09C 1/00 | (2006.01) |
| C09D 11/037 | (2014.01) |
| C08K 3/013 | (2018.01) |

(52) U.S. Cl.
CPC ............ C09C 3/063 (2013.01); C09C 1/0021 (2013.01); C09D 11/037 (2013.01); C09D 157/00 (2013.01); *C01P 2004/61* (2013.01); *C01P 2006/65* (2013.01); *C01P 2006/66* (2013.01); *C08K 3/013* (2018.01); *C09C 2200/1004* (2013.01); *C09C 2200/1054* (2013.01); *C09C 2200/302* (2013.01); *C09C 2200/306* (2013.01); *C09C 2200/409* (2013.01)

(58) Field of Classification Search
CPC .......................... C01P 2006/65; C01P 2006/66
See application file for complete search history.

(56) References Cited

U.S. PATENT DOCUMENTS

| 2007/0034112 A1 | 2/2007 | Mronga et al. |
| 2017/0355855 A1* | 12/2017 | Gruner .................. C09C 1/0015 |
| 2018/0187018 A1 | 7/2018 | Schmid et al. |

FOREIGN PATENT DOCUMENTS

| DE | 44 05 492 A1 | 8/1995 |
| EP | 0 033 457 A2 | 8/1981 |
| EP | 0 688 833 A2 | 12/1995 |
| EP | 0 708 154 A2 | 4/1996 |
| EP | 1 553 144 A1 | 7/2005 |
| EP | 1 682 622 A2 | 7/2006 |
| EP | 1 812 519 A2 | 8/2007 |
| EP | 1 904 587 A2 | 4/2008 |
| JP | 54-81337 A | 6/1979 |
| WO | WO 96/38505 A1 | 12/1996 |
| WO | WO 99/57204 A1 | 11/1999 |
| WO | WO 00/09617 A1 | 2/2000 |
| WO | WO 2005/042643 A1 | 5/2005 |
| WO | WO 2005/049739 A2 | 6/2005 |
| WO | WO 2005/061630 A2 | 7/2005 |
| WO | WO 2011/095341 A | 8/2011 |
| WO | WO 2013/156327 A1 | 10/2013 |
| WO | WO 2015/040537 A | 3/2015 |
| WO | WO-2016097418 A1 * | 6/2016 ........... C09C 1/0015 |
| WO | WO 2017/001393 A1 | 1/2017 |

OTHER PUBLICATIONS

International Search Report dated Oct. 29, 2018 in PCT/EP2018/075289, 4 pages.
International Preliminary Report on Patentability and Written Opinion of the International Searching Authority dated Mar. 31, 2020 in PCT/EP2018/075289 filed Sep. 19, 2018, 9 pages.
W. Ostertag; et al, "Eisenoxidbeschichtete Aluminiumpigmente (Iron oxide coated aluminum pigments)", Farbe + Lack 12 (1987), pp. 973-976 (with English machine translation of Abstract).

* cited by examiner

*Primary Examiner* — Alexandre F Ferre
(74) *Attorney, Agent, or Firm* — Lucas & Mercanti LLP

(57) ABSTRACT

A golden effect pigment comprising an optionally passivated platelet-shaped metallic substrate and an iron oxide layer, wherein the effect pigment has a hue angle $h_{15}$ of $67° \leq h_{15} \leq 78°$ and a chroma $C^*_{15}$ of $\geq 90$ is provided. Further, a golden effect pigment comprising an optionally passivated platelet-shaped metallic substrate and an iron oxide layer, wherein the effect pigment has a hue angle $h_{15}$ of $67° \leq h_{15} \leq 78°$ and a chroma $C^*_{45}$ of $\geq 50$ is provided. The golden effect pigments are highly chromatic and suitable for coloring a coating composition such as a paint, a printing ink, an ink, a varnish, plastics, a fiber, a film or a cosmetic preparation, preferably an automotive, an architectural or an industrial coating composition.

16 Claims, No Drawings

GOLDEN EFFECT PIGMENTS

The present invention relates to a golden effect pigment comprising an optionally passivated platelet-shaped metallic substrate and an iron oxide layer. Further, the invention relates to a process for manufacturing said golden effect pigment by a wet chemical preparation method. Further, the invention relates to a pigment combination comprising said golden effect pigment and a further colored absorption pigment in a specific weight ratio, to an article coated with a composition comprising said golden effect pigment or said pigment combination, and to the use of said golden effect pigment or said pigment combination for coloring a coating composition such as a paint, a printing ink, an ink, a varnish, plastics, a fiber, a film or a cosmetic preparation, preferably an automotive, an architectural or an industrial coating composition.

BACKGROUND OF THE INVENTION

Luster or effect pigments are used in many areas, for example, in automotive coatings, decorative coatings, plastics, paints, printing inks, and cosmetics.

The optical effect is based on the directed reflection of light at predominantly flake-like, parallel-oriented, metallic or strongly refractive pigment particles. Depending on the composition of the pigment platelets, there are interference, reflection and absorption phenomena which create angular-dependent color and lightness effects.

Metallic effect pigments are all made of platelet-shaped substrates known to the skilled person, examples being aluminum platelets/flakes or metal oxide-coated aluminum platelets/flakes. Platelet-shaped aluminum pigments having a coating of iron oxide are well known and described, e.g., in EP-A-0033457 or by W. Ostertag et al., Farbe and Lack 12 (1987) 973-976. They belong to the class of effect pigments which, by virtue of their particular color properties, have found wide use in the coloration of coatings, paints, printing inks, plastics, ceramic compositions and glazes, and cosmetic preparations.

Iron oxide coated aluminum pigments derive their particular optical profile from a combination of specular reflection at the surface of the aluminum platelet, selective light absorption in the iron oxide layer and light interference at the film-like surfaces of the iron oxide layer. Light interference leads to a color which is mainly determined by the thickness of the iron oxide coating layer. Dry pigment powders therefore exhibit the following hues in air with increasing iron oxide layer thickness which are classified as due to $1^{st}$ order or $2^{nd}$ order interference:

$1^{st}$ order interference colors: pale yellow, green-gold, gold, reddish-gold, red, violet, grayish-violet;

$2^{nd}$ order interference colors: yellow, gold, reddish-gold, red-gold, red.

Iron oxide coated metallic flakes, especially aluminum-based flakes are very bright and opaque, that is why they are widely used in automotive coatings. The pigments customarily used in this field are based on aluminum platelets and exhibit a metallic mirror effect. Iron oxide coated aluminum pigments are known for brilliant colors in the golden to red color area.

Iron oxide layers of effect pigments can be provided on the metallic substrate particles by gas phase decomposition of volatile iron compounds in the presence of oxygen and/or water vapor (so-called chemical vapor deposition) or by a wet-chemical coating process (e.g., sol-gel or precipitation process).

EP-A-0033457 describes a process for the preparation of colored effect pigments comprising a metallic substrate whose surface is at least partially covered with an iron oxide, wherein iron pentacarbonyl is oxidized to iron oxide in a fluidized bed of the metallic substrates with oxygen at above 100° C. Effect pigments of a bright-golden to reddish golden interference color are obtained. They show, for example, in an alkyd melamine resin a golden color exhibiting high brilliance and color purity.

US-A-2007/0034112 discloses luster pigments based on aluminum platelets which are coated with iron oxide by chemical vapor deposition. The aluminum platelets have an average size of from 8 to 30 µm, an average thickness of from 300 to 600 nm and an aspect ratio of from 15 to 70. Pigments are described which, when applied in a coating, exhibit a gold, orange or red interference color.

In wet-chemical preparation methods, metal oxide containing layers can be applied by hydrolytic reaction of appropriate metal salts, e.g., iron(III) salts such as iron(III) chloride, sulfate or nitrate, or hydrolysable organometallic compounds. Details about the preparation of a metal oxide coating layer on a metal-based substrate of an effect pigment are provided, e.g., in EP-A-0708154 or JP-A-54081337.

WO-A-2013/156327 discloses a wet-chemical preparation process, wherein an initially formed hydroxyl-containing metal oxide layer on an aluminum or aluminum alloy substrate is subjected to a liquid post-treatment medium at a temperature of at least 90° C.

EP-A-1553144 discloses reddish interference pigments based on $Fe_2O_3/SnO_2/[Al(P)]$), obtained by a wet chemical process. The pigments show a higher chroma than pigments without an intermediate binder layer of hydrated tin oxide.

WO-A-00/09617 discloses, for example, a multilayer pigment having a light golden luster which is based on aluminum powder (31.7%) and coated with a silica layer (52.0%), followed by a $SnO_2$ layer (2.0%) and a final $Fe_2O_3$ layer (14.3%). Additionally, a multilayer pigment is described having a copper-golden metallic luster which is based on 32.3% of brass, 53.7% of $SiO_2$ and 14.0% of $Fe_2O_3$.

WO-A-2005/061630 discloses a $SiO_2$-coated aluminum pigment with a coating of FeOOH resulting in a golden yellow, lustrous powder.

Effect pigments of the golden color range can be divided into neutral golden effect pigments having a hue angle $h_{15}$ (in face angle) of about 73°±5°, greenish golden effect pigments having a hue angle $h_{15}$ of about 83°±5° and reddish golden effect pigments having a hue angle $h_{15}$ of about 63°±5°.

Golden effect pigments are of great value as styling tools in various applications, since they offer high chroma, gloss and hiding power. These properties allow highly chromatic automotive paints having good gloss and hiding power. By mixing with suitable colored absorption pigments various gold shades are possible.

However, the pigments known from the prior art have still some shortcomings in the neutral golden color space. For example, the chroma and/or lightness is/are insufficient for advanced applications. Especially in the field of the coatings industry, mainly automotive coatings, there is a requirement for ever thinner paint/coating layers with further improved coloristic properties. Accessing new color spaces in combination with good performance properties like hiding, appearance and fastness in terms of weathering and humidity resistance may be achieved by means of pigments having a high hiding power, high chroma and/or high lightness. Since there is a commercial interest in various applications, mainly coating applications, of higher brilliance, higher chroma and better hiding power in the golden color space, there is a continuing need for providing improved, especially more chromatic, golden effect pigments to increase the accessible color space.

Therefore, it is an object of the present invention to provide a golden effect pigment having improved coloristic properties, especially improved chroma and optionally improved lightness, while good hiding power may be retained.

A further object of the present invention is to provide a pigment combination comprising a golden effect pigment, said pigment combination exhibiting improved coloristic properties in coating applications, especially improved chroma and optionally improved lightness, while good hiding power may be retained, in coating applications, especially in orange- to red-hued or greenish coatings, preferably automotive coatings.

SUMMARY OF THE INVENTION

It has now been found that a golden effect pigment comprising an optionally passivated platelet-shaped metallic substrate and an iron oxide layer shows improved coloristic properties, especially a significantly improved chroma.

The admixture of a further colored absorption pigment especially of an orange to red-hued or greenish color tone enables a coating having superior coloristic properties compared to a pigment combination comprising a golden effect pigment of the prior art.

Accordingly, in a first aspect the invention relates to a golden effect pigment comprising an optionally passivated platelet-shaped metallic substrate and an iron oxide layer, wherein the effect pigment has a hue angle $h_{15}$ of $67°\leq h_{15}\leq 78°$ and a chroma $C^*_{15}$ of $\geq 90$.

In a further aspect, the invention relates to a golden effect pigment comprising an optionally passivated platelet-shaped metallic substrate and an iron oxide layer, wherein the effect pigment has a hue angle $h_{15}$ of $67°\leq h_{15}\leq 78°$ and a chroma $C^*_{45}$ of $\geq 50$.

In a further aspect, the invention relates to a method of manufacturing a golden effect pigment, as defined herein, which method comprises (a) providing an optionally passivated platelet-shaped metallic substrate, and (b) coating the substrate in a liquid medium comprising an iron oxide precursor compound.

In a further aspect, the invention relates to a pigment combination comprising (a) a golden effect pigment comprising an optionally passivated platelet-shaped metallic substrate and an iron oxide layer, wherein the effect pigment has a hue angle $h_{15}$ of $67°\leq h_{15}\leq 78°$ and a chroma $C^*_{15}$ of $\geq 90$;

(b) a colored absorption pigment, (c) optionally a further effect pigment;

wherein the weight ratio of the golden effect pigment (a) to pigment (b) and optional pigment (c) is of from 95:5 to 5:95, preferably 80:20 to 5:95, more preferably 75:25 to 20:80.

In a further aspect, the invention relates to the use of a golden effect pigment or a pigment combination, each as defined herein, for coloring a coating composition such as a paint, a printing ink, an ink, a varnish, plastics, a fiber, a film or a cosmetic preparation, preferably an automotive, an architectural or an industrial coating composition.

In a further aspect, the invention relates to an article coated with a composition comprising a golden effect pigment or a pigment combination, each as defined herein; and to an automotive coating, which is colored with a golden effect pigment or a pigment combination, each as defined herein.

DETAILED DESCRIPTION OF THE INVENTION

Color may be described in different color space systems. As used herein, the color data like C* (chroma), h (hue angle), L* (lightness), a* (red-green axis) and b* (yellow-blue axis) are understood as defined in the CIELAB color measuring system (specified by the Commission Internationale de Eclairage). For example, considering a point A in the CIELAB color space, it is defined by the three coordinates L*, a* and b*. The chromaticity coordinates a* and b* may also be expressed by way of cylindrical coordinates C* and h, as known to one skilled in the art.

The term "golden effect pigment" means an effect pigment having a neutral golden interference color.

The term "hue angle $h_{15}$" used herein means the hue angle in the L*C*h color space (also referred to as CIELAB) specified by the Commission Internationale de l' Eclairage. The values are measured at an observation angle of 15°.

The term "chroma $C^*_{15}$" used herein means the chroma in the L*C*h color space (also referred to as CIELAB) specified by the Commission Internationale de l' Eclairage. The values are measured at an observation angle of 15°. Chroma $C^*_{45}$ and $C^*_{75}$, resp., are measured at an observation angle of 45° and 75°, resp.

The values are determined on panels with a dried and cured coating film comprising a 20 µm basecoat/40 µm clearcoat system, obtained by pneumatic spray application onto an aluminum panel, wherein the basecoat in full shade is formed by applying a conventional solvent-borne, medium solids cellulose acetobutyrate (CAB)/polyester varnish having a pigment/binder weight ratio of 20:100 and drying at room temperature, followed by applying a 1K clearcoat and drying at about 135° C. The colorimetric evaluations are then performed on these panels using a mufti-angle colorimeter BYK-MAC (from BYK Gardner) with a constant incident angle of 45° and illuminant D65. The values h, C*, L*, a* and b* are measured at observation angles of 15°, −15° (relative to the specular angle) and at higher angles of 25°, 45°, 75° and 110°.

The term "iron oxide" used herein means α-iron(III) oxide in particular. However, the term "iron oxide" also comprises mixtures of α-iron(III) oxide with minor amounts of γ-iron(III) oxide, magnetite ($Fe_3O_4$), hydrated iron oxide or iron oxide hydroxide (e.g., FeO(OH), $Fe_2O_3.H_2O$, $Fe_2O_3.nH_2O$ with n≥2, Fe(OH)$_3$, Fe(OH)$_2$ or a mixture of two or more of these hydroxyl-containing iron-oxides). Preferably, Fe atoms are present as Fe(III). However, within the present invention Fe atoms may also be present as Fe(II). Preferably, the iron oxide layer comprises $Fe_2O_3$.

The term "colored absorption pigment" used herein means a colored pigment excluding white pigments, like titanium oxide (C.I. Pigment White 6), or any effect pigment, i.e., pigments which exhibit directed reflection at predominantly two-dimensional, oriented metallic or highly refractive particles.

The term "a mixture thereof" or "a combination thereof" means any possible, physically blended mixture or combination of two or more components mentioned in the respective list, either of the same or different kind of components.

The term "platelet" or "flake" means those substrates having an aspect ratio of 10:1 or higher.

The $d_{50}$ value in the cumulative frequency distribution of the volume-averaged size distribution function (median diameter, particle size distribution), as is obtained by laser scattering methods, indicates that 50% of the golden effect pigments have a diameter which is the same as or smaller than the respectively indicated value. In this case, the size distribution curve is determined using an instrument from Malvern Instruments Ltd. (Mastersizer 3000) in accordance with manufacturer indications. The sample is typically prepared by dispersing the sample to be analysed in 2-propanol for a few minutes by use of ultrasound of the dispersion unit.

Preferably, the invention relates to a golden effect pigment comprising an optionally passivated platelet-shaped metallic substrate and an iron oxide layer, wherein the effect pigment has a hue angle $h_{15}$ of $67°\leq h_{15}\leq 78°$ and a chroma $C^*_{15}$ of $\geq 90$, wherein the values $h_{15}$ and $C^*_{15}$ are determined on panels with a dried and cured coating film comprising a 20 µm basecoat/40 µm clearcoat system, obtained by pneumatic spray application onto an aluminum panel, wherein the basecoat in full shade is formed by applying a solvent-borne, medium solids cellulose acetobutyrate (CAB)/polyester varnish having a pigment/binder weight ratio of 20:100 and drying at room temperature, followed by applying a 1K clearcoat and drying at about 135° C.; using a multi-angle colorimeter with a constant incident angle of 45° and D65 illuminant.

Especially, the golden effect pigment has a hue angle $h_{15}$ of $67°<h_{15}<78°$.

Also preferred is a golden effect pigment having a chroma $C^*_{15}$ of $\geq 95$, more preferred $C^*_{15}\geq 100$, most preferred of $C^*_{15}\geq 110$, and especially $C^*_{15}\geq 120$.

The median diameter $d_{50}$ of the golden effect pigment may be varied over a range. Preferably, the golden effect pigment has a median diameter of 8 µm$\leq d_{50}\leq 22$ µm.

The median diameter $d_{50}$ of the golden effect pigment may be, for example, in the range of 8 µm$\leq d_{50}\leq 12.5$ µm. Alternatively, the median diameter $d_{50}$ may be in the range of 13 µm$\leq d_{50}\leq 22$ µm.

Accordingly, in a preferred aspect, the golden effect pigment has a median diameter $d_{50}$ of 8 µm$\leq d_{50}\leq 12.5$ µm, preferably of 8.5 µm$\leq d_{50}\leq 12$ µm.

Further preferably, the golden effect pigment has a median diameter $d_{50}$ of 13 µm$\leq d_{50}\leq 22$ µm, more preferably of 14 µm$\leq d_{50}\leq 21$ µm.

Further preferred is a golden effect pigment, wherein the effect pigment has a median diameter of 13 µm$\leq d_{50}\leq 22$ µm and has a chroma $C^*_{15}$ of $\geq 110$, more preferably the golden effect pigment has a median diameter of 14 µm$\leq d_{50}\leq 21$ µm and has a chroma $C^*_{15}$ of $\geq 110$.

Especially preferred is golden effect pigment, wherein the effect pigment has a median diameter of 13 µm$\leq d_{50}\leq 22$ µm and has a chroma $C^*_{15}$ of $\geq 120$, more preferably the golden effect pigment has a median diameter of 14 µm$\leq d_{50}\leq 21$ µm and has a chroma $C^*_{15}$ of $\geq 120$.

In a further aspect, the invention relates to a golden effect pigment comprising an optionally passivated platelet-shaped metallic substrate and an iron oxide layer, wherein the effect pigment has a hue angle $h_{15}$ of $67°\leq h_{15}\leq 78°$ and a chroma $C^*_{45}$ of $\geq 50$, preferably a hue angle $h_{15}$ of $67°<h_{15}<78°$ and a chroma $C^*_{45}$ of $\geq 50$.

A preferred effect pigment is a golden effect pigment comprising an optionally passivated platelet-shaped metallic substrate and an iron oxide layer, wherein the effect pigment has a hue angle $h_{15}$ of $67°\leq h_{15}\leq 78°$ and a chroma $C^*_{45}$ of $\geq 50$, and the effect pigment has a median diameter of 8 µm$\leq d_{50}\leq 12.5$ µm.

Especially preferred is a golden effect pigment comprising an optionally passivated platelet-shaped metallic substrate and an iron oxide layer, wherein the effect pigment has a hue angle $h_{15}$ of $67°\leq h_{15}\leq 78°$ and a chroma $C^*_{45}$ of $\geq 55$, more preferably a chroma $C^*_{45}$ of $\geq 58$, and the effect pigment has a median diameter of 8 µm$\leq d_{50}\leq 12.5$ µm.

In a further aspect, the invention relates to a golden effect pigment comprising an optionally passivated platelet-shaped metallic substrate and an iron oxide layer, wherein the effect pigment has a hue angle $h_{15}$ of $67°\leq h_{15}\leq 78°$ and a chroma $C^*_{75}$ of $\geq 30$.

A preferred effect pigment is a golden effect pigment comprising an optionally passivated platelet-shaped metallic substrate and an iron oxide layer, wherein the effect pigment has a hue angle $h_{15}$ of $67°\leq h_{15}\leq 78°$ and a chroma $C^*_{75}$ of $\geq 30$, and the effect pigment has a median diameter of 8 µm$\leq d_{50}\leq 12.5$ µm.

The metallic substrates may be of a wide range of metals used in the field of effect pigments. The metallic substrate is usually in the form of platelets or flakes. The metallic substrate may be selected from aluminum, steel, silver, copper, gold-bronze (brass), zinc, zirconium, tin, titanium, alloys thereof, and combinations thereof. The metallic substrates are preferably aluminum-based, iron, copper or gold-bronze.

More preferably, the metallic substrate is an aluminum-based substrate. Appropriate aluminum-based substrate particles are generally known to the skilled person. The aluminum-based substrate particles may be made of an aluminum core or aluminum alloy core which may be at least partly coated with one or more passivation layers.

The aluminum or aluminum alloy core is usually in the form of platelets or flakes. As an exemplary aluminum alloy, aluminum bronze may be mentioned.

The aluminum or aluminum alloy platelets or flakes may be obtained by means of PVD techniques (PVD: Physical Vapor Deposition) or by common atomizing and grinding techniques. Suitable aluminum or aluminum alloy platelets are produced, for example, by the Hall process by wet grinding in white spirit. The starting material is an atomized, irregular aluminum grit which is ball-milled in white spirit and in the presence of lubricant into platelet-shaped particles and subsequently classified. Also, dry grinding of aluminum powder is possible.

The metallic substrate is more preferably aluminum. The aluminum substrate may be of the "cornflake" type or of the "silver dollar" type depending on the quality and shape of the starting granules and on the milling conditions.

Alternatively, the aluminum platelets may be produced via PVD techniques, also known as VMP (Vacuum Metallized Pigment). Aluminum is coated preferably in vacuum on a plastic foil pre-prepared with a release layer. By dissolving the release layer aluminum flakes are usually produced which are further sized down by mechanical impact like stirring and classified to the desired particle diameter. The average thickness of thus produced flakes is generally about 5 to 100 nm, preferably about 10 to 50 nm. Usually, thus prepared flakes show uniform thickness distribution and high hiding power.

Average thickness and average particle size of the metallic substrates, especially the aluminum or aluminum alloy platelets, may be varied over a broad range.

Typically, the average geometric thickness of the metallic platelets, especially aluminum-based platelets, may be within the range of 10 nm to 1500 nm, preferably 70 to 1000 nm, more preferably 80 to 800 nm, and most preferably 80 to 500 nm.

The thickness of the platelets is usually determined by transmission electron microscopy (TEM) or scanning electron microscopy (SEM) produced on cross-cuts of about 100 flakes. For this purpose, a thin film of a coating containing the aligned flakes is cut and analysed Via SEM or TEM, wherein the geometric thickness values of about 100 platelets are investigated and averaged statistically.

The average diameter of the platelets, especially aluminum or aluminum alloy platelets, may be within the range of 3 to 100 nm, preferably 5 to 50 µm. Typically, the aspect ratio of average diameter to average thickness may be within the range of 10:1 to 1000:1. The diameter may be determined by laser scattering size determinations.

The metal platelets, especially the aluminum or aluminum alloy platelets, have typically a BET surface area of from 0.5 to 80 $m^2/g$, preferably 0.8 to 50 $m^2/g$.

As mentioned above, the aluminum or aluminum alloy core of the aluminum-based substrate particles may at least partially be coated with one or more passivation layers, for example completely coated with one or more passivation layers. Preferably, the one or more passivation layers cover the aluminum-based platelets completely, including the side faces.

Appropriate passivating layers are generally known to the skilled person. The passivating layer is preferably an inorganic layer such as a metal phosphate layer, or an inorganic oxide layer. If the inorganic passivating layer is a metal phosphate layer, the metal may be selected from Ti, V, Cr, Mn, Fe, Co, Ni, Cu, Zn, Al, Zr, Nb, Mo, Ta or W. If the inorganic passivating layer is an inorganic oxide layer, the oxide may be selected from Ti, V, Cr, Mn, Fe, Co, Ni, Cu, Zn, Al, Zr, Nb, Mo, Ta, W, Ge, Si, Sn and Bi oxides or any combination thereof.

Preferably, the passivating layer is a metal phosphate layer, a silica layer, an aluminum oxide layer, a hydrated aluminum oxide (AlOOH) layer or a combination thereof. More preferably, the passivating layer is a silica layer or a metal phosphate layer, most preferably a silica layer.

The geometric thickness of the passivating layer, as, for example, obtainable by a wet-chemical process, may be varied. Usually, the geometric thickness of a passivating layer is about 20 to about 100 nm, preferably 30 to 80 nm. The geometric layer thickness may be determined on the basis of TEM micrographs (cross-cuts).

According to a preferred aspect, the invention relates to a golden effect pigment, wherein the effect pigment comprises an aluminum substrate which is passivated with a layer of a metal phosphate, silica, aluminum oxide, hydrated aluminum oxide or a combination thereof.

According to the invention an iron oxide layer is applied on an optionally passivated platelet-shaped metallic substrate, preferably an optionally passivated aluminum-based platelet-shaped substrate. The iron oxide layer may be produced by a wet-chemical method, as described later. The wet chemical coating process is generally performed until the desired interference color is obtained. A thermal treatment transfers the hydroxyl-containing iron oxide layer into a $Fe_2O_3$-containing layer. The desired final hue after thermal treatment $h_{15}$ is 73°±5°.

Preferably, the optionally passivated metallic platelet-shaped substrates are completely encapsulated by the iron oxide layer.

The geometric thickness of the iron oxide coating, as, for example, obtainable by a wet-chemical process, usually is about 60 to about 160 nm, preferably 70 to 160 nm, more preferably 70 to 150 nm. The geometric layer thickness may be determined on the basis of TEM micrographs (cross-cuts).

Preferably, the golden effect pigment has only one iron oxide layer. Especially, the golden effect pigment does not have a further metal oxide layer of high refractive index, i.e., having a refractive index of >1.8.

The iron oxide layer may be doped with up to 10 wt % of other metals, like aluminum or zirconium or the like, based on the total amount of iron and doping metal atoms in the metal-doped iron oxide layer. The doping metal concentration in the iron oxide layer may be determined by TEM in combination with EDXS (energy dispersive X-ray spectroscopy), as mentioned, for example, in WO-2015/040537.

Preferably, the iron oxide layer may be doped with up to 10 wt % of aluminum, based on the total amount of iron and aluminum atoms in the aluminum-doped iron oxide layer. Preferably, the aluminum-doped iron oxide layer contains from 0.05 wt % to 10 wt % Al or from 0.5 to 8 wt % or from 0.5 to 6 wt %, based on the total amount of Fe and Al atoms in the Al-doped iron oxide layer.

Usually, the Al concentration in the substrate-near part of the Al-doped iron-oxide layer is higher than the Al concentration in the substrate-remote part of the Al-doped iron oxide layer.

In the present invention, it is possible that the iron oxide layer represents the outermost layer of the golden effect pigment. Alternatively, one or more additional layers may be applied onto the iron oxide layer, such as a $SiO_2$ layer, a polymer layer, an organosilane layer, or any combination thereof.

The geometric thickness of the final layer may be 2 to about 50 nm, preferably 2 to 30 nm, more preferably 2 to 20 nm, dependent on the kind of surface modification.

Accordingly, in a preferred aspect, the invention relates to a golden effect pigment comprising an optionally passivated platelet-shaped aluminum-based substrate and an iron oxide layer, wherein the effect pigment has a hue angle $h_{15}$ of $67° \leq h_{15} \leq 78°$ and a chroma $C^*_{15}$ of $\geq 90$, wherein the iron oxide layer is the final layer.

Alternatively preferred is a golden effect pigment comprising an optionally passivated platelet-shaped aluminum-based substrate and an iron oxide layer, wherein the effect pigment has a hue angle $h_{15}$ of $67° \leq h_{15} \leq 78°$ and a chroma $C^*_{15}$ of $\geq 90$, wherein the effect pigment comprises one or more additional layers on the iron oxide layer, wherein the one or more additional layers are preferably selected from a silica layer, a polymer layer, an organosilane layer, or any combination or mixtures thereof.

In a preferred embodiment, the golden effect pigment contains a final layer which is selected from a $SiO_2$ layer, a polymer layer, an organosilane layer, or combinations thereof. The term "final layer" is synonymous to the "outermost layer". Such surface modification is usually adapted to the particular end-use. With such final layer, surface polarity of the golden effect pigment may be adjusted, which in turn may improve bonding of the effect pigment to a binder system, for example, of a paint or an ink.

For the pigment surface modification step, the effect pigment may be provided in a liquid medium containing at least one surface-modifying agent. However, it is also possible to bring the surface-modifying agent into contact with the effect pigment of a calcination step Via the gas phase.

Methods for surface modification of effect pigments and appropriate surface modifying agents such as silanes having surface-reactive functional groups (e.g., alkoxysilanes etc.) are known to the skilled person and may improve compatibility of the effect pigment with the varnish or lacquer. Surface modification methods and agents are described, for example, in EP-A-1682622, EP-A-1904587, WO-A-99/57204, EP-A-1812519 or EP-A-0688833.

The golden effect pigment may be manufactured by coating optionally passivated platelet-shaped metallic substrates by a wet chemical method of hydrolytic decomposition of an iron(III) salt in a liquid medium.

Accordingly, a further aspect of the invention relates to a method of manufacturing a golden effect pigment, as described in any aspect herein, which method comprises (a) providing an optionally passivated platelet-shaped metallic substrate, and (b) coating the substrate in a liquid medium comprising an iron oxide precursor compound.

Preferably, the golden effect pigment obtained or obtainable by the method of the present invention corresponds to the golden effect pigment, as described herein.

Methods for preparing a passivating layer on a metallic substrate such as aluminum platelets are generally known to the skilled person.

In principle, a passivating layer may be produced by a wet-chemical method or a chemical vapor deposition (CVD) method. For example, aluminum pigments passivated with a layer of aluminum oxide and/or hydrated aluminum oxide are described in WO-A-96/38505 or WO-A-2005/049739.

In the wet-chemical process, appropriate precursor compounds such as organic silicon and/or aluminum compounds in which the organic groups are bonded to the metals Via oxygen atoms are typically hydrolyzed in the presence of the substrate particles (e.g., aluminum flakes or platelets) and of an organic solvent in which the metal compounds are soluble. Preferably, a metal alkoxide (especially tetraethoxysilane and aluminum triisopropoxide) is hydrolyzed with water in the presence of an alcohol (e.g., ethanol or 2-propanol) and a basic and/or acid catalyst.

Basic catalysts are, for example, aqueous ammonia and/or amines, acid catalysts may be, for example, phosphoric acid or organic acids like acetic acid or oxalic acid. This is preferably done by initially charging substrate particles, ethanol, water and ammonia, heating this mixture to from 40° C. to 90° C., with stirring and continuously adding a solution of the metal alkoxide in ethanol and water or aqueous ammonia. Following a subsequent stirring time of usually from 1 to 15 hours, the mixture is cooled down to room temperature, and the coated pigment is isolated by filtering off, washing and optionally drying. Further details about the method of preparing a passivating layer on aluminum are provided, e.g., in EP-A-0708154, DE-A-4405492 or WO-A-2011/95341.

The iron oxide layer is usually prepared by a wet-chemical method, for example, by hydrolysis of suitable iron oxide precursor compounds. The coating process is generally performed until the desired interference color is obtained. A thermal treatment transfers the hydroxyl-containing iron oxide layer into a $Fe_2O_3$-containing layer, preferably a hematite layer. The desired final hue after thermal treatment $h_{15}$ is 73°±5°.

As indicated above, the substrate is coated in a liquid medium, which comprises an iron oxide precursor compound. Usually, the liquid medium is an aqueous medium, typically containing water in an amount of from 10 to 100 wt % or from 30 to 100 wt %, based on the total amount of liquids in the aqueous medium.

In case of a doped iron oxide layer, the liquid medium of step a) includes the further metal compound, for example, an aluminum compound. Aluminum compounds may be aluminum salts such as aluminum sulfate, aluminum halides, aluminum nitrate, aluminum phosphate, hydrolysable aluminum compounds such as aluminum alkoxides or mixtures thereof.

The iron oxide precursor compound which may be used for providing an iron oxide layer Via wet chemical process are generally known to the skilled person. Exemplary iron oxide precursor compounds are, for example, iron salts such as iron(III) halides (e.g., $FeCl_3$), iron(III) nitrate, iron(III) sulfate, hydrolysable iron compounds such as iron alkoxides, complex compounds of iron such as iron acetylacetonate or any combination or mixture thereof.

In principle, the iron oxide layer may be applied onto the substrate at acidic or basic pH. Preferably, the liquid medium has a pH or 5 or less, more preferably 4 to 2. Preferably, the pH of the aqueous medium is kept constant while applying the iron-oxide layer or the Al-doped iron oxide layer on the substrate. The temperature may be varied over a broad range, such as at least 20 to 100° C.

Preferably, the pigment obtained in step b) is subsequently subjected to a thermal treatment step, for example, for drying the pigment and/or effecting further condensation in the iron oxide layer. The thermal treatment step may be carried out by calcination at about 250 to 450° C., preferably 280 to 400° C., for at least 5 min, for example within a period of about 10 to 60 min. Alternatively, the effect pigment obtained in step b) may be subjected to a medium comprising one or more high boiling solvents and heating at a temperature of at least 90° C. for at least 0.5 hours.

High boiling solvents usually have a boiling point of from 90 to 400° C., more preferably 100 to 300° C. Examples may be monohydroxy) alcohols, diols or polyols, glycol ethers, polyglycol ethers, polyethylene glycol monoethyl ethers, polypropylene glycols, aldehydes, esters, carbonate esters, organic acids, amides, lactams such as NMP, ketones, ethers, alkanes, halide-substituted alkanes, aromatic compounds, liquid polymers, mineral oils, or mixtures thereof.

Usually, the golden effect pigment is isolated by known methods, like filtering or by thermal treatment, possibly in combination, and used as a paste.

Accordingly, in a further aspect, the invention relates to a golden effect pigment, as defined herein, obtainable by a method, which method comprises (a) providing an optionally passivated platelet-shaped metallic substrate, and (b) coating the substrate in a liquid medium comprising an iron oxide precursor compound.

For various applications, the golden effect pigment may be suitably used in a blend with any further pigment, preferably a colored absorption pigment and optionally a conventional effect pigment, which is different from the present golden effect pigment, to provide a pigment combination.

The pigment combination of the present invention consists of at least two or three components, wherein the effect pigment (a) is the golden effect pigment, as defined herein, the second pigment (b) is at least one colored absorption pigment, and the optional third pigment (c) is a further effect pigment.

Generally, pigment (b) may be at least one pigment other than an effect pigment or a white pigment. Pigment (b) may be any pigment of any color tone, preferably a pigment having a yellow or red-hued or greenish color tone. A combination with other colored pigments like a black or brown pigment may also be possible to achieve the effect.

Preferably, the colored absorption pigment (b) is any transparent colored absorption pigment of a color tone ranging from green to yellow to violet or even blue dependent on the desired shade of the application, preferably of the desired coating.

A combination with other colored pigments like a black or brown pigment may also be possible, for example, a transparent carbon black pigment or transparent black perylene pigments.

The term "transparent pigment" used herein means a pigment that provides coatings which are substantially transparent in the range of 400 to 700 nm, without appreciable scattering of radiation in such wavelengths.

Pigment (b) may be an organic pigment, an inorganic pigment or a mixture thereof.

Preferably, pigment (b) has a color tone suitable to shade the present effect pigment, like yellow, red-hued or greenish.

Accordingly, in a preferred aspect, pigment (b) is at least one transparent pigment, especially selected from the group consisting of an organic pigment, an inorganic pigment and a mixture thereof.

Organic colored absorption pigments suitable for the present pigment combination typically comprise organic color and black pigments. Suitable examples include a pigment selected from the group consisting of a monoazo, disazo, disazo condensation, anthanthrone, anthraquinone, anthrapyrimidine, benzimidazolone, quinacridone, quinophthalone, diketopyrrolopyrrole, dithioketopyrrolopyrrole, dioxazine, flavanthrone, indanthrone, isoindoline, isoindolinone, isoviolanthrone, metal complex, perinone, perylene, phthalocyanine, pyranthrone, pyrazoloquinazolone, indigo, thioindigo, triarylcarbonium pigment and a mixture thereof, including a solid solution or a mixed crystal thereof.

Suitable examples include the following:

Monoazo pigments: C.I. Pigment Yellow 1, 3, 62, 65, 73, 74, 97, 183 and 191; C.I. Pigment Orange 5, 38 and 64; C.I. Pigment Red 1, 2, 3, 4, 5, 23, 48:1, 48:2, 48:3, 48:4, 49, 49:1, 51, 51:1, 52:1, 52:2, 53, 53:1, 53:3, 57:1, 58:2, 58:4, 63, 112, 146, 148, 170, 184, 187, 191:1, 210, 245, 247 and 251;

Disazo pigments: C.I. Pigment Yellow 12, 13, 14, 16, 17, 81, 83, 106, 113, 126, 127, 155, 170, 174, 176 and 188; C.I. Pigment Orange 16, 34 and 44;

Disazocondensation pigments: C.I. Pigment Yellow 93, 95 and 128; C.I. Pigment Red 144, 166, 214, 220, 221, 242 and 262; C.I. Pigment Brown 23 and 41;

Anthanthrone pigments: C.I. Pigment Red 168;

Anthraquinone pigments: C.I. Pigment Yellow 147 and 199; C.I. Pigment Red 177;

Anthrapyrimidine pigments: C.I. Pigment Yellow 108;

Benzimidazolone pigments: C.I. Pigment Yellow 120, 151, 154, 180, 181; C.I. Pigment Orange 36 and 72, C.I. Pigment Red 175, 185, 208; C.I. Pigment Violet 32; C.I. Pigment Brown 25;

Quinacridone pigments: C.I. Pigment Orange 48 and 49; C.I. Pigment Red 122, 202, 206 and 209; C.I. Pigment Violet 19;

Quinophthalone pigments: C.I. Pigment Yellow 138;

Diketopyrrolopyrrole pigments: C.I. Pigment Orange 71, 73 and 81; C.I. Pigment Red 254, 255, 264, 270 and 272;

Dioxazine pigments: C.I. Pigment Violet 23 and 37;

Flavanthrone pigments: C.I. Pigment Yellow 24;

Indanthrone pigments: C.I. Pigment Blue 60 and 64;

Isoindoline pigments: C.I. Pigment Yellow 139 and 185; C.I. Pigment Orange 61 and 69, C.I. Pigment Red 260;

Isoindolinone pigments: C.I. Pigment Yellow 109, 110 and 173;

Isoviolanthrone pigments: C.I. Pigment Violet 31;

Metal complex pigments: C.I. Pigment Red 257; C.I. Pigment Yellow 117, 129, 150, 153 and 177; C.I. Pigment Green 8;

Perinone pigments: C.I. Pigment Orange 43; C.I. Pigment Red 194;

Perylene pigments: C.I. Pigment Red 123, 149, 178, 179 and 224; C.I. Pigment Violet 29;

Phthalocyanine pigments: C.I. Pigment Blue 15, 15:1, 15:2, 15:3, 15:4, 15:6, 16; C.I. Pigment Green 7, 36;

Pyranthrone pigments: C.I. Pigment Orange 51; C.I. Pigment Red 216;

Pyrazoloquinazolone pigments: C.I. Pigment Orange 67 and C.I. Pigment Red 216;

Indigo pigments: C.I. Pigment Red 282;

Thioindigo pigments: C.I. Pigment Red 88 and 181; C.I. Pigment Violet 38;

Triarylcarbonium pigments: C.I. Pigment Red 81, 81:1 and 169; C.I. Pigment Violet 1, 2, 3 and 27; C.I. Pigment Blue 1, 61 and 62; C.I. Pigment Green 1;

C.I. Pigment Yellow 101 (Aldazin yellow);

C.I. Pigment Brown 22.

Preferably, the organic pigment is a yellow to red-hued, green or blue organic pigment, for example a yellow, green, blue, red or orange organic pigment, i.e., a C.I. Pigment Green, C.I. Pigment Yellow, C.I. Pigment Red or C.I. Pigment Orange, selected from an anthraquinone, diketopyrrolopyrrole, isoindolinone, metal complex, perinone, perylene, phthalocyanine pigment, indigo pigment or any mixture thereof, including a solid solution or a mixed crystal.

Especially preferred are C.I. Pigment Yellow 129, Pigment Yellow 110, Pigment Red 168, Pigment Red 177, Pigment Red 179, Pigment Red 282 and any diketopyrrolopyrrole pigment like Pigment Orange 73, Pigment Red 254, Pigment Red 255, Pigment Red 264, Pigment Red 270 or Pigment Red 272.

Suitable organic pigments are, for example, commercially available under the trademarks Irgazin® Cosmoray Orange L 2950, Irgazin Rubine L 4030, Irgazin DPP Orange RA, Irgazin Red L 3630, Irgazin Yellow L 2040, Irgazin Yellow L 0800, Paliogen® Red L 3885, Paliogen Red L 3920, Heliogen® Blue L 6950 or Heliogen Green L 9361.

Suitable inorganic pigments may be a transparent yellow iron oxide pigment (C.I. Pigment Yellow 42), a transparent red iron oxide pigment (C.I. Pigment Red 101) or a mixture thereof.

Suitable inorganic black or brown pigments may be carbon black (C.I. Pigment Black 7), graphite (C.I. Pigment Black 10) or chrome iron oxide (C.I. Pigment Brown 29).

Suitable inorganic pigments are, for example, commercially available under the trademark Sicotrans®.

The colored absorption pigment (b) is preferably transparent.

Additionally, an opaque colored absorption pigment may be used in small amounts for special effects, generally in an amount less than 10 wt %, preferably less than 5 wt %, based on the weight of all pigments in the composition.

The pigments used herein are preferably present in finely dispersed form. Typically, the organic pigments have an average primary particle size of 200 nm or less, preferably about 80 to 200 nm. The inorganic pigments typically have an average particle size of 200 nm or less, preferably about 80 to 200 nm. The average particle size may be determined according to DIN ISO 13320:2009.

Effect pigment (c) may be any conventional effect pigment known in the art. Effect pigment (c) may be a metal pigment like aluminum flakes or an effect pigment based on transparent substrates, like natural mica, synthetic mica or glass flakes. The transparent substrates are typically coated with one or more layers of metal oxides like $TiO_2$, $TiO_2$ (doped with $SnO_2$), $SiO_2$ and/or $Fe_2O_3$ or the like. Preferred are pigments which reflect due to interference and absorption phenomena of thin films golden to red light. The metallic golden gloss of the opaque golden effect pigment of the invention can thus be modified with especially semi-transparent pigments in a similar color. The coloristic effect is an enrichment of a (two-dimensional) metallic gloss with so-called deepness in a third dimension.

Suitable effect pigments (c) are, for example, commercially available under the trademark Lumina® or Mearin®.

The weight ratio of the golden effect pigment (a) to colored absorption pigment (b) and optional effect pigment (c) may be varied in a wide range.

In a further aspect, the invention relates to a pigment combination comprising (a) a golden effect pigment comprising an optionally passivated platelet-shaped metallic substrate and an iron oxide layer, wherein the effect pigment has a hue angle $h_{15}$ of $67° \leq h_{15} \leq 78°$ and a chroma $C^*_{15}$ of $\geq 90$;

(b) a colored absorption pigment, and (c) optionally a further effect pigment;

wherein the weight ratio of the golden effect pigment (a) to pigment (b) and pigment (c) is of from 95:5 to 5:95, preferably 80:20 to 5:95, more preferably 75:25 to 20:80.

The weight ratio of the golden effect pigment (a) to pigment (b) and optional pigment (c) is, for example, 95:5, i.e., the amount of 95 wt % corresponds to the golden effect effect pigment, and the amount of 5 wt % corresponds to the combination of pigments (b) and (c). The weight ratio of pigment (b) and pigment (c) may be of from 100:0 to 50:50, preferably 75:25 to 60:40.

Preferably, pigment (b) is a transparent pigment, especially selected from the group consisting of an organic pigment, an inorganic pigment and a mixture thereof.

In particular, the organic pigment is a yellow or red-hued organic pigment, for example, a yellow to red-hued, green or blue organic pigment selected from an anthraquinone, diketopyrrolopyrrole, isoindolinone, metal complex, perinone, perylene, phtalocyanine, indigo pigment or any mixture thereof, including a solid solution or a mixed crystal.

The inorganic pigment may be a transparent yellow iron oxide pigment (C.I. Pigment Yellow 42), a transparent red iron oxide pigment (C.I. Pigment Red 101) or a mixture thereof.

Pigment (c) may be an effect pigment selected from metal pigments, or effect pigments based on a transparent substrate selected from natural mica, synthetic mica or glass. Preferably, pigment (c) comprises a platelet-shaped substrate selected from natural mica, synthetic mica or glass, which is coated with one or more layers of metal oxides selected from $TiO_2$, $TiO_2$ (doped with $SnO_2$), $SiO_2$ and/or $Fe_2O_3$.

Metal pigments may be aluminum-based platelets, preferably aluminum platelets.

The golden effect pigment (a) may be incorporated into the application system in a customary manner, for example as a slurry or paste.

Accordingly, the present invention provides a composition comprising the golden effect pigment.

The pigment combination may be incorporated into the application system in a customary manner. The golden effect pigment (a), as defined herein, may be added as a slurry as well as the optional effect pigment (c). Usually, pigment (b) is added in a pre-dispersed state.

The present effect pigment or the present pigment combination is outstandingly suitable for all pigment end-use applications, especially coloring organic or inorganic materials of natural and synthetic origin, for example, a) for mass coloring polymers, e.g., in the form of resins, rubber or plastics including films and fibers;

b) for the preparation of paints, paint systems, coating compositions, for example, in automotive, architectural and industrial coating compositions, c) for inks, printing inks, e.g., digital printing like ink-jet printing, as well as for toners in electrophotography, e.g., for laser printers;

d) as an additive to colorants, such as pigments and dyes;

e) for cosmetic preparations; and the like.

Paints are aqueous or solvent-borne coating materials, in which the instant pigment combination may be employed. Organic film-forming binders that may be used include all of the binders that are usual in the coatings sector. Examples of binder materials which may be colored with the golden effect pigment or the pigment combination, as defined herein, include more particularly:

oil-based materials (based on linseed oil or polyurethane oils), cellulose-based materials (NC, CAB, CAP), materials based on chlorinated rubber, vinyl materials (based on PVC, PVDF, VC copolymer, polyvinyl acetate, polyvinyl ester dispersion, polyvinyl alcohol, polyvinyl acetal, polyvinyl ether, polystyrene, styrene copolymers), acrylic materials, alkyd materials, saturated polyester materials, unsaturated polyester materials, polyurethane materials (one pack, two pack), epoxy materials, silicone materials.

The systems are described in detail in D. Stoye, W. Freitag, Paints, Coatings and Solvents, Second Edition, 1998, Wiley-VCH.

Preferably, the golden effect pigment or the present pigment combination is used in waterborne and solvent-borne coating applications, more preferably in decorative coating compositions like architectural, automotive or industrial coating compositions, for example for any consumer goods.

The golden effect pigment or the present pigment combination is generally incorporated into their respective application media in a customary way. An article may then be coated with these application media thus pigmented. Said article may be, for example, a vehicle body, an industrial equipment, an architectural facing element, etc.

In case of plastics, the golden effect pigment or the present pigment combination may also be incorporated for coloring into the application medium in the mass. The articles comprise the golden effect pigment or the present pigment combination.

Suitable compositions for the cosmetic preparations into which the golden effect pigment may be introduced are known in the art. The formulations of cosmetics using the golden effect pigment of the invention are accomplished by measures and methods familiar to the skilled person. The golden effect pigment or the present pigment combination may be suitably used, for example, in nail varnishes.

The golden effect pigment or the present pigment combination may be used in an appropriate amount dependent on the application. It may range of from 0.01 to 30% by weight, preferably 0.01 to 15% by weight, based on the total weight of the material to be colored in the wet state.

In a further aspect, the invention relates to the use of the golden effect pigment or the pigment combination, as defined in any aspect herein, for coloring or pigmenting coating composition such as a paint, a printing ink, an ink, a varnish, plastics, a fiber, a film or a cosmetic preparation, preferably an automotive, an architectural or an industrial coating composition.

The coating composition may be any decorative coating composition like an automotive, an architectural or an industrial coating composition or a paint. The coating composition, printing ink, ink or paint may be waterborne or solvent-borne.

Preferably, the golden effect pigment or the present pigment combination is used as a colorant for an automotive, architectural, industrial coating composition, a paint, a printing ink, an ink or plastics. In particular, the golden effect pigment or the present pigment combination is used as a colorant for an automotive OEM or refinish coating composition.

In a further aspect, the invention relates to a coating composition including a paint, a printing ink, an ink, a varnish, plastics, a fiber, a film or a cosmetic preparation, which is colored or pigmented with a golden effect pigment or a pigment combination, as defined in any aspect herein.

In a further aspect, the invention relates to an article coated with a composition comprising a golden effect pigment or a pigment combination, as defined in any aspect herein.

Any material of the article may be coated with the composition comprising the golden effect pigment or the present pigment combination, including such materials as glass, ceramics, plastics, smooth-surfaced composites and metallic substrates.

Especially, the composition is particularly adapted for metallic articles or plastic articles. The article may be bare substrate material or, in the case of metal substrates, may be pretreated to impart corrosion resistance as by phosphatizing, or electrocoating like cathodic dip coating, or other similar treatments well known in the art.

A coating comprising the golden effect pigment or the present pigment combination is especially suitable for a multilayer coating used in the automotive industry. The golden effect pigment or the present pigment combination is usually incorporated into the basecoat layer of a basecoat/clearcoat coating system, as known in the art.

Accordingly, the invention relates to an automotive coating, which is colored or pigmented with a golden effect pigment or a pigment combination, as defined in any aspect herein.

In a further aspect, the invention relates to a process for coloring or pigmenting a coating composition such as a paint, a printing ink, an ink, a varnish, plastics, a fiber, a film or a cosmetic preparation, preferably an automotive, an architectural or an industrial coating composition, which method comprises adding thereto a golden effect pigment or a pigment combination, as defined herein.

The golden effect pigment of the invention is excellent in its coloristic properties, especially a significantly higher chroma compared to neutral golden effect pigments of the prior art may be achieved, while the hiding power may be retained. The golden effect is highly chromatic with well-balanced sparkle effect. The pigments show golden-metallic luster. The strongly increased chroma is mainly observed at −15°, 15°, and 25°, the so-called face angle.

In addition, the golden effect pigments show high chroma at observation angles at 45° and 75° resulting in golden effect pigments showing also higher chroma in the down flop.

Especially, golden effect pigments having a smaller medium diameter of 8 to 12 µm offer coatings of a smooth appearance having a high homogeneity, good gloss and high distinctness of images combined with high chroma.

Further, the pigment combination of the invention is excellent in its coloristic properties, in particular in chroma. The admixture of an especially transparent colored absorption pigment (b), especially of a yellow to violet color tone or a greenish color tone, and optionally a further effect pigment to the golden effect pigment (a) enables a coating having superior coloristic properties compared to a similar pigment combination with a neutral golden effect pigment known in the prior art. The coatings are more brilliant expressed by a combination of a higher chroma and optionally higher lightness and good hiding power.

Including further effect pigments (c) which reflect due to interference and absorption phenomena of thin films golden to red light, the metallic golden gloss of the opaque golden effect pigment of the invention can thus be modified with especially semitransparent effect pigments (c) in a similar color. The coloristic effect is an enrichment of a (two-dimensional) metallic gloss with so-called deepness in a third dimension.

Further, the performance characteristics like weather fastness and light fastness needed for exterior use coatings are not adversely affected.

Thus, the golden color space can be increased in combination with good performance properties like hiding, appearance and fastness in terms of weathering and humidity resistance.

The definitions and preferences given for the pigment mentioned herein-before apply in any combination as well as in any combination for the other aspects of the invention.

The present invention will now be explained in more detail with reference to the following examples. These examples should not be construed as limited. Unless otherwise stated, "%" is always % by weight (wt %).

EXAMPLES

In order to determine the CIELAB values of hue h [°], chroma C* and lightness L*, the dried and cured coating films obtained (in masstone) are applied and measured as follows: the pigment(s) is/are incorporated (as a 50:50 slurry of pigment(s) in a solvent which is part of the varnish) by stirring with a level of total pigmentation of 5 wt % (based on the total weight of the wet varnish) into a conventional solvent-borne, medium solids cellulose acetobutyrate (CAB)/polyester varnish (pigment/binder 20/100), until the pigments are finally dispersed. The completed varnish is applied by pneumatic spray application onto aluminum panels with a wet film thickness of about 150 to 160 µm and subsequently dried at room temperature. After drying, the basecoat is overcoated by a 1K clearcoat, dried and cured at 135° C. After curing the basecoat is of about 20 µm and the clearcoat is of about 40 µm. The color data are determined using a mufti-angle colorimeter BYK-MAC (from BYK Gardner) with a constant incident angle of 45° and D65 illuminant. The values C*, L*, a*, b* and h are measured at 15°, −15° (relative to the specular angle) and in higher angles of 25°, 45°, 75° and 110°.

Example 1

206 g of a passivated aluminum paste in ethanol (solids content of 60 wt %, $SiO_2$ content of 26 wt %, $d_{50}$=15.4 µm (passivated aluminum)) were suspended in 1.17 L of water. The suspension was heated to 78° C. within 1 hour, and the pH value was adjusted to 2.8 by adding $Al_2(SO_4)_3$ and 5% $HNO_3$. By adding 812 g of an aqueous 50 wt % iron nitrate solution to the suspension a hydroxyl-containing iron(III) nitrate layer was applied while keeping the pH value using aqueous 25% NaOH. The resulting suspension was stirred for about 1 hour, followed by cooling to room temperature, the obtained product was filtered, washed with water and 2-propanol and calcined at 300° C. for 20 min.

Example 2

Example 1 was repeated apart from 875 g of an aqueous 50 wt % iron nitrate instead of 812 g.

Example 3

223 g of a passivated aluminum paste in ethanol (solids content of 52 wt %, $SiO_2$ content of 24 wt %, $d_{50}$=15 μm (passivated aluminum)) were suspended in 1.23 L of water. The suspension was heated to 78° C. within 1 hour, and the pH value was adjusted to 2.8 by adding $Al_2(SO_4)_3$ and 5% $HNO_3$. By adding 875 g of an aqueous 50 wt % iron nitrate solution to the suspension a hydroxyl-containing iron(III) nitrate layer was applied while keeping the pH value using aqueous 25% NaOH. The resulting suspension was stirred for about 30 min, followed by cooling to room temperature, the obtained product was filtered, washed with water and 2-propanol and calcined at 300° C. for 20 min.

Example 4

230 g of a passivated aluminum paste in ethanol (solids content of 55 wt %, $SiO_2$ content of 25 wt %, $d_{50}$=15.2 μm (passivated aluminum)) were suspended in 1.29 L of water and coated according to the procedure of Example 2. Samples were removed after adding 844 g (4a) and 875 g (4b) of aqueous 50 wt % iron nitrate solution. The obtained products were filtered, washed with water and 2-propanol and calcined at 300° C. for 20 min.

Example 5

230 g of a passivated aluminum paste in ethanol (solids content of 60 wt %, $SiO_2$ content of 25 wt %, $d_{50}$=15.8 μm (passivated aluminum) were suspended in 1.3 L of water. The suspension was heated to 78° C. within 1 hour, and the pH value was adjusted to 2.8 by adding $Al_2(SO_4)_3$ and 5% $HNO_3$. By adding 950 g of an aqueous 50 wt % iron nitrate solution to the suspension hydroxyl-containing iron(III) nitrate layer was applied while keeping the pH value using aqueous 25% NaOH. The resulting suspension was stirred for 1 hour, followed by cooling to room temperature, the obtained product was filtered, washed with water and 2-propanol. The product was suspended in a solvent of a boiling point of above 260° C., and the suspension was heated to 190-220° C. for 6 hours.

Example 6

Aluminum platelets ($d_{50}$=15.2 μm; BET surface area=3.5 $m^2/g$) were passivated according to the method described in Example 1 (step a)) of EP-A-0708154 yielding passivated aluminum platelets having a $SiO_2$ content of 25 wt %. 160 g of said passivated aluminum paste in ethanol (solids content of 47 wt %) were suspended in 700 mL of water. The suspension was heated to 78° C. within 1 hour, and the pH value was adjusted to 2.8 by adding $Al_2(SO_4)_3$ and 5% $HNO_3$. By adding 635 g of an aqueous 50 wt % iron nitrate solution a hydroxyl-containing iron(III) oxide layer was applied while keeping the pH value using aqueous 25% NaOH. The obtained suspension was cooled to room temperature, and the obtained product was filtered, washed with water and 2-propanol and calcined at 300° C. for 20 min. The product obtained was suspended in a solvent of a boiling point of above 260° C., and the suspension was heated to 200° C. for 12 hours.

Example 7

Aluminum platelets ($d_{50}$=11.4 μm; BET surface area=5.6 $m^2/g$) were passivated according to the method described in Example 1 (step a)) of EP-A-0708154 yielding passivated aluminum platelets having a $SiO_2$ content of 26 wt %. 93 g of said passivated aluminum paste (solids content of 57 wt %) were suspended in 700 mL of water. The suspension was heated to 78° C. within 1 hour, and the pH value was adjusted to 2.8 by adding $Al_2(SO_4)_3$ and 5% $HNO_3$. By adding an aqueous 50 wt % iron nitrate solution to the suspension a hydroxyl-containing iron(III) oxide layer of a golden color tone was applied while keeping the pH value using aqueous 25% NaOH. The resulting suspension was cooled to room temperature, and the obtained product was filtered, washed with water and 2-propanol, and the obtained product was suspended in a solvent of a boiling point of above 260° C., and the suspension was heated to 200° C. for 12 hours.

Example 8

Aluminum platelets ($d_{50}$=10.3 μm; BET surface area=7.4 $m^2/g$) were passivated according to the method described in Example 1 (step a)) of EP-A-0708154 yielding passivated aluminum platelets having a $SiO_2$ content of 48 wt %. 78 g of said passivated aluminum paste (solids content of 60 wt %) were suspended in 700 mL of water. The suspension was heated to 78° C. within 1 hour, and the pH value was adjusted to 2.8 by adding $Al_2(SO_4)_3$ and 5% $HNO_3$. By adding 423 g of an aqueous 50 wt % iron nitrate solution to the suspension a hydroxyl-containing iron(III) oxide layer was applied while keeping the pH value using aqueous 25% NaOH. The resulting suspension was cooled to room temperature, and the obtained product was filtered, washed with water and 2-propanol, and the obtained product was suspended in a solvent of a boiling point of above 260° C., and the suspension was heated to 200° C. for 12 hours.

Example 9

Aluminum platelets ($d_{50}$=11.4 μm; BET surface area=5.3 $m^2/g$) were passivated according to the method described in Example 1 (step a)) of EP-A-0708154 yielding passivated aluminum platelets having a $SiO_2$ content of 50 wt %. 86 g of said passivated aluminum paste (solids content of 64 wt %) were suspended in 700 mL of water. The suspension was heated to 78° C. within 1 hour, and the pH value was adjusted to 2.8 by adding $Al_2(SO_4)_3$ and 5% $HNO_3$. By adding 540 g of an aqueous 50 wt % iron nitrate solution to the suspension a hydroxyl-containing iron(III) oxide layer was applied while keeping the pH value using aqueous 25% NaOH. The resulting suspension were cooled to room temperature, and the obtained product was filtered, washed with water and 2-propanol, and the obtained product was suspended in a solvent of a boiling point of above 260° C., and the suspension was heated to 200° C. for 12 hours.

Example 10

Aluminum platelets ($d_{50}$=9.1 μm; BET surface area=7.4 m$^2$/g) were passivated according to the method described in Example 1 (step a)) of EP-A-0708154 yielding passivated aluminum platelets having a SiO$_2$ content of 32 wt %. 79 g of said passivated aluminum paste (solids content of 51 wt %) were suspended in 700 mL of water. The suspension was heated to 78° C. within 1 hour, and the pH value was adjusted to 2.8 by adding Al$_2$(SO$_4$)$_3$ and 5% HNO$_3$. By adding 620 g of an aqueous 50 wt % iron nitrate solution to the suspension a hydroxyl-containing iron(III) oxide layer was applied while keeping the pH value using aqueous 25% NaOH. The resulting suspension was cooled to room temperature, and the obtained product was filtered, washed with water and 2-propanol, and the obtained product was suspended in a solvent of a boiling point of above 260° C., and the suspension was heated to 200° C. for 12 hours.

Example 11

Aluminum platelets ($d_{50}$=8.4 μm; BET surface area=7.0 m$^2$/g) were passivated according to the method described in Example 1 (step a)) of EP-A-0708154 yielding passivated aluminum platelets having a SiO$_2$ content of 55 wt %. 88 g of said passivated aluminum paste (solids content of 48 wt %) were suspended in 700 mL of water. The suspension was heated to 78° C. within 1 hour, and the pH value was adjusted to 2.8 by adding Al$_2$(SO$_4$)$_3$ and 5% HNO$_3$. By adding 526 g of an aqueous 50 wt % iron nitrate solution to the suspension a hydroxyl-containing iron(III) oxide layer was applied while keeping the pH value using aqueous 25% NaOH. The resulting suspension was cooled to room temperature, and the obtained product was filtered, washed with water and 2-propanol, and the obtained product was suspended in a solvent of a boiling point of above 260° C., and the suspension was heated to 200° C. for 12 hours.

Example 12

Aluminum platelets ($d_{50}$=11 μm; BET surface area=5.9 m$^2$/g) were passivated according to the method described in Example 1 (step a)) of EP-A-0708154 yielding passivated aluminum platelets having a SiO$_2$ content of 35 wt %. 88 g of said passivated aluminum paste (solids content of 57 wt %) were suspended in 700 mL of water. The suspension was heated to 78° C. within 1 hour, and the pH value was adjusted to 2.8 by adding Al$_2$(SO$_4$)$_3$ and 5% HNO$_3$. By adding 596 g of an aqueous 50 wt % iron nitrate solution to the suspension a hydroxyl-containing iron(III) oxide layer was applied while keeping the pH value using aqueous 25% NaOH. The resulting suspension was cooled to room temperature, and the obtained product was filtered, washed with water and 2-propanol, and the obtained product was suspended in a solvent of a boiling point of above 260° C., and the suspension was heated to 200° C. for 12 hours.

The coloristic data are shown in Tables 1 to 3.

A difference of 1 unit in C* may already be recognized by a person skilled in the art.

Comparative Example 1: Paliocrom® Brilliant Gold L 2054 (based on aluminum flakes of silver dollar type coated with Fe$_2$O$_3$ having a surface modification)

Comparative Example 2: Paliocrom® Brilliant Gold L 2050 (based on aluminum flakes of silver dollar type coated with Fe$_2$O$_3$)

Comparative Example 3: Paliocrom® Gold L 2020 (based on aluminum flakes of cornflake-type coated with Fe$_2$O$_3$)

TABLE 1

| Observation angle 15° | | | | | |
|---|---|---|---|---|---|
| Examples | h [°] | C* | L* | a* | b* |
| Comp. Ex. 1 | 73.76 | 85.08 | 114 | 23.8 | 81.68 |
| Comp. Ex. 2 | 74.29 | 82.32 | 107.8 | 22.29 | 79.24 |
| Comp. Ex. 3 | 73.34 | 78.93 | 98.9 | 22.63 | 75.61 |
| 1 | 77.04 | 125.1 | 114.41 | 28.06 | 121.92 |
| 2 | 71.98 | 128.56 | 110.71 | 39.77 | 122.26 |
| 3 | 74.45 | 126.23 | 113.74 | 33.83 | 121.61 |
| 4a | 76.56 | 127.62 | 112.89 | 29.66 | 124.13 |
| 4b | 73.55 | 129.95 | 110.83 | 36.81 | 124.63 |
| 5 | 72.82 | 139.3 | 115.3 | 41.77 | 133.1 |
| 6 | 77.6 | 130.1 | 115.1 | 27.93 | 127 |
| 7 | 76.33 | 119.8 | 108.1 | 28.32 | 116.4 |
| 8 | 76.65 | 116.2 | 101.9 | 26.84 | 113.1 |
| 9 | 76.25 | 114.9 | 97.61 | 27.33 | 111.7 |
| 10 | 76.55 | 99.83 | 90.72 | 23.23 | 97.09 |
| 11 | 74.06 | 106.1 | 88.6 | 29.15 | 102.1 |
| 12 | 74.62 | 120.3 | 102.1 | 31.91 | 116 |

TABLE 2

| Observation angle 45° | | | | | |
|---|---|---|---|---|---|
| Examples | h [°] | C* | L* | a* | b* |
| Comp. Ex. 1 | 73.56 | 40.75 | 47.82 | 11.53 | 39.08 |
| Comp. Ex. 2 | 73.44 | 44.15 | 50.55 | 12.59 | 42.32 |
| Comp. Ex. 3 | 73.72 | 43.83 | 49.97 | 12.29 | 42.07 |
| 1 | 74.54 | 55.04 | 47.36 | 14.67 | 53.05 |
| 2 | 68.64 | 52.48 | 43.99 | 19.11 | 48.87 |
| 3 | 71.8 | 52.67 | 44.71 | 16.45 | 50.04 |
| 4a | 74.11 | 59.67 | 48.05 | 16.33 | 57.39 |
| 4b | 70.57 | 57.89 | 45.78 | 19.29 | 54.68 |
| 5 | 69.56 | 53.14 | 40.39 | 18.5 | 49.79 |
| 6 | 75.86 | 64.33 | 48.72 | 15.45 | 48.72 |
| 7 | 74.38 | 60.47 | 49.58 | 16.28 | 58.23 |
| 8 | 74.43 | 64.37 | 51.2 | 17.27 | 62.01 |
| 9 | 74.33 | 64.02 | 50.25 | 17.29 | 61.64 |
| 10 | 75.25 | 63.85 | 51.23 | 16.25 | 61.75 |
| 11 | 71.93 | 64.38 | 49.34 | 19.97 | 61.21 |
| 12 | 72.88 | 62.38 | 49.11 | 18.36 | 59.62 |

TABLE 3

| Observation angle 75° | | | | | |
|---|---|---|---|---|---|
| Examples | h [°] | C* | L* | a* | b* |
| Comp. Ex. 1 | 67.92 | 26.22 | 22.48 | 9.86 | 24.3 |
| Comp. Ex. 2 | 68.45 | 28.95 | 25.1 | 10.63 | 26.92 |
| Comp. Ex. 3 | 70.03 | 29.08 | 26.63 | 9.93 | 27.33 |
| 1 | 67.04 | 31.88 | 25.97 | 12.43 | 29.35 |
| 2 | 62.71 | 31.31 | 24.61 | 14.36 | 27.83 |
| 3 | 66.6 | 30.94 | 23.83 | 12.29 | 28.4 |
| 4a | 67.54 | 34.97 | 24.99 | 13.36 | 32.32 |
| 4b | 64.64 | 34.91 | 23.78 | 14.65 | 30.89 |
| 5 | 63.17 | 31.02 | 21.6 | 14.27 | 27.86 |
| 6 | 69.01 | 37.96 | 26.23 | 13.6 | 35.44 |
| 7 | 66.47 | 33.06 | 25.59 | 13.2 | 30.31 |
| 8 | 68.35 | 37.86 | 27.21 | 13.97 | 35.19 |
| 9 | 69.71 | 39.11 | 29.03 | 13.57 | 36.69 |
| 10 | 71.13 | 41.87 | 30.39 | 13.54 | 39.62 |
| 11 | 67.15 | 40.24 | 29.01 | 15.63 | 37.08 |
| 12 | 67.39 | 34.75 | 26.69 | 13.36 | 32.08 |

Example 13

A pigment combination comprising Example 5 and Paliogen Red L 3885 (C.I. Pigment Red 179) in a weight ratio of 50:50 is formed.

Example 14

A pigment combination comprising Example 5 and Irgazin Cosmoray Orange L 2950 (a diketopyrrolopyrrole pigment) in a weight ratio of 50:50 is formed.

Example 15

A pigment combination comprising Example 5 and Irgazin Yellow L0800 (C.I. Pigment Yellow 129) in a weight ratio of 50:50 is formed.

Example 16

A pigment combination comprising Example 5, Metallux 2194 (Aluminum flakes), Cromophtal Brown L 3001 (5R) (C.I. Pigment Brown 23) and Sicotrans Yellow L 1916 (C.I. Pigment Yellow 129) in a weight ratio of 45:5:40:10 is formed.

Example 17

A pigment combination comprising Example 5, Lumina Royal Ext Copper 3903H (interference pigment based on mica flakes coated with $Fe_2O_3/SiO_2/TiO_2$), Paliogen Red L 3885 in a weight ratio of 45:15:40 is formed.

Example 18

A pigment combination comprising Example 5, Heliogen Green L 9361 (C.I. Pigment Green 36) and Irgazin Yellow L0800 (C.I. Pigment Yellow 129) in a weight ratio of 40:40:20 is formed.

Example 19

A pigment combination comprising Example 5, Heliogen Blue L 6950 (C.I. Pigment Blue 15.1), Sicopal Yellow and Irgazin Yellow L0800 (C.I. Pigment Yellow 129) in a weight ratio of 40:35:20:5 is formed.

Example 20

A pigment combination comprising Example 12 and Paliogen Red L 3885 (Ci. Pigment Red 179) in a weight ratio of 50:50 is formed.

Example 21

A pigment combination comprising Example 12 and Irgazin Cosmoray Orange L 2950 (a diketopyrrolopyrrole pigment) in a weight ratio of 50:50 is formed.

Example 22

A pigment combination comprising Example 12 and Irgazin Yellow L0800 (Ci. Pigment Yellow 129) in a weight ratio of 50:50 is formed.

Comparative Examples 4 to 6

Examples 14 to 16 were repeated apart from using the pigment of Comparative Example 1 instead of the pigment of Example 5.

Comparative Examples 7 to 10

Examples 16 to 19 were repeated apart from using the pigment of Comparative Example 2 instead of the pigment of Example 5.

Comparative Examples 11 to 13

Examples 20 to 22 were repeated apart from using the pigment of Comparative Example 1 instead of the pigment of Example 12.

The results are demonstrated in Table 4 to 6.

TABLE 4

Observation angle 15°

| Examples | h | C* | L* | a* | b* |
|---|---|---|---|---|---|
| Comp. Ex. 4 | 45.03 | 96.02 | 60.7 | 67.86 | 67.94 |
| 13 | 50.21 | 107.6 | 58.49 | 68.83 | 82.65 |
| Comp. Ex. 5 | 60.1 | 121.6 | 87.82 | 60.6 | 105.4 |
| 14 | 62.03 | 140.5 | 86.11 | 65.87 | 124.1 |
| Comp. Ex. 6 | 75.01 | 123.6 | 92.89 | 31.97 | 119.4 |
| 15 | 73.03 | 137.5 | 90.09 | 40.12 | 131.5 |
| Comp. Ex. 7 | 53.23 | 67.91 | 71.79 | 40.65 | 54.4 |
| 16 | 52.08 | 70.93 | 68.52 | 43.59 | 55.95 |
| Comp. Ex. 8 | 47.83 | 99.34 | 67.67 | 66.69 | 73.62 |
| 17 | 50.99 | 110.5 | 62.61 | 69.53 | 85.83 |
| Comp. Ex. 9 | 103.37 | 93.33 | 84.78 | −21.58 | 90.81 |
| 18 | 97 | 96.54 | 73.68 | −11.77 | 95.82 |
| Comp. Ex. 10 | 124.1 | 29.01 | 47 | −16.25 | 24.03 |
| 19 | 99.29 | 36.6 | 40.23 | −5.91 | 36.12 |

TABLE 5

Observation angle 45°

| Examples | h | C* | L* | a* | b* |
|---|---|---|---|---|---|
| Comp. Ex. 11 | 38.39 | 48.81 | 21.3 | 38.26 | 30.31 |
| 20 | 41.82 | 56.35 | 24.72 | 41.99 | 37.58 |
| Comp. Ex. 12 | 57.18 | 57.18 | 35.3 | 31 | 48.06 |
| 21 | 57.46 | 63.55 | 37.31 | 34.18 | 53.57 |
| Comp. Ex. 13 | 78.87 | 61.02 | 41.62 | 11.78 | 59.88 |
| 22 | 73.85 | 68.17 | 43.48 | 18.96 | 65.48 |

TABLE 6

Observation angle 75°

| Examples | h | C* | L* | a* | b* |
|---|---|---|---|---|---|
| Comp. Ex. 11 | 29.86 | 32.75 | 12 | 28.4 | 16.3 |
| 20 | 33.9 | 40.01 | 15.53 | 33.21 | 22.32 |
| Comp. Ex. 12 | 53.73 | 39.85 | 23.43 | 23.57 | 32.13 |
| 21 | 53.34 | 43.95 | 25.17 | 26.24 | 35.26 |
| Comp. Ex. 13 | 83.7 | 36.9 | 25.73 | 4.05 | 36.67 |
| 20 | 75.87 | 43.02 | 28.65 | 10.5 | 41.72 |

The invention claimed is:
1. A golden effect pigment comprising:
a passivated platelet-shaped aluminum or aluminum alloy substrate and an iron oxide layer,
wherein the effect pigment has a hue angle $h_{15}$ of $67° \leq h15 \leq 78°$ and a chroma $C^*_{15}$ of $\geq 90$.

2. The golden effect pigment according to claim 1, wherein the platelet-shaped aluminum or aluminum alloy substrate is passivated with a layer of a metal phosphate, silica, aluminum oxide, hydrated aluminum oxide or a combination thereof.

3. The golden effect pigment according to claim 1, wherein the golden effect pigment has a median diameter $d_{50}$ of 8 µm≤$d_{50}$≤22 µm.

4. The golden effect pigment according to a claim 1, wherein the golden effect pigment has a median diameter of 8 µm≤$d_{50}$≤12.5 µm or 13 µm≤$d_{50}$≤22 µm.

5. The golden effect pigment according to claim 1, wherein the iron oxide layer has an average thickness of 60 to 160 nm.

6. The golden effect pigment according to claim 1, wherein the golden effect pigment has a median diameter of 13 µm≤$d_{50}$≤22 µm and has a chroma $C^*_{15}$ of ≥110.

7. The golden effect pigment according to claim 1, wherein the golden effect pigment comprises one or more additional layers on the iron oxide layer.

8. The golden effect pigment according to claim 7, wherein the one or more additional layers are at least one selected from the group consisting of a silica layer, an organosilane layer and a polymer layer.

9. A pigment combination comprising:
(a) the golden effect pigment of claim 1;
(b) a colored absorption pigment; and
(c) optionally a further effect pigment;
wherein a weight ratio of the golden effect pigment (a) to pigment (b) and optional pigment (c) is of from 95:5 to 5:95.

10. A colored coating composition, comprising the golden effect pigment according to claim 1,
wherein the coating composition comprises a paint, a printing ink, an ink, a varnish, plastics, a fiber, a film or a cosmetic preparation.

11. An article coated with a composition comprising the golden effect pigment of claim 1.

12. An automotive coating, which is colored with the golden effect pigment of claim 1.

13. A method of manufacturing the golden effect pigment according to claim 1, the method comprising:
(a) providing a passivated platelet-shaped aluminum or aluminum alloy substrate, and
(b) coating the passivated platelet-shaped aluminum or aluminum alloy substrate in a liquid medium comprising an iron oxide precursor compound.

14. A method of coloring a coating composition comprising a paint, a printing ink, an ink, a varnish, plastics, a fiber, a film or a cosmetic preparation, the method comprising:
adding thereto the golden effect pigment of claim 1.

15. A golden effect pigment comprising:
a passivated platelet-shaped aluminum or aluminum alloy substrate and an iron oxide layer,
wherein the golden effect pigment has a hue angle $h_{15}$ of 67°≤$h_{15}$≤78° and a chroma $C^*_{45}$ of ≥50.

16. The golden effect pigment according to claim 15, wherein the golden effect pigment has a median diameter of 8 µm≤$d_{50}$≤12.5 µm.

* * * * *